(12) United States Patent
Harris

(10) Patent No.: US 8,560,582 B2
(45) Date of Patent: Oct. 15, 2013

(54) METHOD FOR ANALYZING RECORDS IN A DATA BASE

(76) Inventor: Jeffrey Saul Harris, Mill Valley, CA (US)

( * ) Notice: Subject to any disclaimer, the term of this patent is extended or adjusted under 35 U.S.C. 154(b) by 601 days.

(21) Appl. No.: 10/216,268

(22) Filed: Aug. 12, 2002

(65) Prior Publication Data
US 2004/0030669 A1    Feb. 12, 2004

(51) Int. Cl.
G06F 15/16   (2006.01)
G06F 12/00   (2006.01)
G06F 17/30   (2006.01)
G06Q 50/00   (2012.01)

(52) U.S. Cl.
USPC ............................... 707/899; 705/2; 709/250

(58) Field of Classification Search
USPC ............... 707/6, 3, 104.1; 717/124; 705/2, 3; 600/300
See application file for complete search history.

(56) References Cited

U.S. PATENT DOCUMENTS

| | | | |
|---|---|---|---|
| 5,005,143 A | 4/1991 | Altschuler et al. | |
| 5,255,187 A | 10/1993 | Sorensen | |
| 5,331,550 A | 7/1994 | Stafford et al. | |
| 5,437,278 A | 8/1995 | Wilk | |
| 5,471,382 A | 11/1995 | Tallman et al. | |
| 5,551,436 A | 9/1996 | Yago | |
| 5,574,828 A | 11/1996 | Hayward et al. | |
| 5,594,638 A | 1/1997 | Iliff | |
| 5,619,990 A | 4/1997 | Kanai | |
| 5,666,953 A | 9/1997 | Wilk | |
| 5,711,297 A | 1/1998 | Iliff | |
| 5,724,968 A | 3/1998 | Iliff | |
| 5,764,923 A | 6/1998 | Tallman et al. | |
| 5,772,585 A | 6/1998 | Lavin et al. | |
| 5,809,476 A | 9/1998 | Ryan | |
| 5,823,948 A | 10/1998 | Ross, Jr. et al. | |
| 5,839,438 A | 11/1998 | Graettinger et al. | |
| 5,839,439 A | 11/1998 | Nierlich et al. | |
| 5,845,254 A | 12/1998 | Lockwood et al. | |
| 5,974,124 A | 10/1999 | Schlueter, Jr. et al. | |
| 6,014,631 A | 1/2000 | Teagarden et al. | |
| 6,029,138 A | 2/2000 | Khorasani et al. | |
| 6,047,259 A | 4/2000 | Campbell et al. | |
| 6,108,635 A | 8/2000 | Herren et al. | |
| 6,154,739 A * | 11/2000 | Wrobel .............................. 707/6 |
| 6,230,048 B1 * | 5/2001 | Selvester et al. .............. 600/523 |
| 6,256,613 B1 * | 7/2001 | Falchuk et al. .................... 705/2 |
| 6,302,844 B1 | 10/2001 | Walker et al. | |
| 6,468,210 B1 | 10/2002 | Iliff | |
| 6,475,143 B2 | 11/2002 | Iliff | |
| 6,484,144 B2 * | 11/2002 | Martin et al. ...................... 705/2 |
| 6,505,196 B2 | 1/2003 | Drucker et al. | |
| 6,523,009 B1 | 2/2003 | Wilkins | |
| 6,551,243 B2 * | 4/2003 | Bocionek et al. ............. 600/300 |
| 6,587,849 B1 | 7/2003 | Mason et al. | |
| 6,704,723 B1 * | 3/2004 | Alavi et al. ........................ 707/3 |
| 6,735,551 B2 | 5/2004 | Voegeli et al. | |
| 6,763,517 B2 * | 7/2004 | Hines ............................ 717/124 |
| 7,418,399 B2 * | 8/2008 | Schaeffer et al. ................. 705/2 |
| 2002/0046346 A1 | 4/2002 | Evans | |

(Continued)

*Primary Examiner* — Susan Chen
(74) *Attorney, Agent, or Firm* — Curtis, Neil & Elwood, LLC

(57) ABSTRACT

A method for analyzing records in a data base which collects predetermined data and creates or appends a record, assigns individual conditions to homogeneous groups, retrieves rules, applies the rules to the data, reviews results generated from applying the rules to the data and generates at least one message.

10 Claims, 4 Drawing Sheets

(56) References Cited

U.S. PATENT DOCUMENTS

| | | |
|---|---|---|
| 2002/0049612 A1 | 4/2002 | Jaeger et al. |
| 2002/0077849 A1 | 6/2002 | Baruch et al. |
| 2002/0082862 A1 | 6/2002 | Kelley et al. |
| 2002/0087358 A1 | 7/2002 | Gilbert |
| 2002/0133375 A1 | 9/2002 | Moore et al. |
| 2002/0133377 A1 | 9/2002 | Brown |
| 2002/0133379 A1 | 9/2002 | Lewis et al. |
| 2002/0138304 A1 | 9/2002 | Fontanesi |
| 2002/0138306 A1 | 9/2002 | Sabovich |
| 2002/0147614 A1 | 10/2002 | Doerr et al. |
| 2002/0147615 A1 | 10/2002 | Doerr et al. |
| 2002/0152096 A1 | 10/2002 | Falchuk et al. |
| 2002/0165735 A1 | 11/2002 | Stangel |
| 2002/0165737 A1 | 11/2002 | Mahran |
| 2002/0168512 A1 | 11/2002 | Eggers et al. |
| 2002/0169636 A1 | 11/2002 | Eggers et al. |
| 2002/0169637 A1 | 11/2002 | Akers et al. |
| 2002/0188466 A1 | 12/2002 | Barrette et al. |
| 2002/0188467 A1 | 12/2002 | Eke |
| 2002/0194028 A1 | 12/2002 | Johnston et al. |
| 2002/0194029 A1 | 12/2002 | Guan et al. |
| 2002/0198742 A1 | 12/2002 | Kameda et al. |
| 2003/0018240 A1 * | 1/2003 | Goetzke et al. ............... 600/300 |
| 2003/0040662 A1 | 2/2003 | Keys |
| 2003/0046114 A1 | 3/2003 | Davies et al. |
| 2003/0050802 A1 | 3/2003 | Jay et al. |
| 2003/0050803 A1 | 3/2003 | Marchosky |
| 2003/0055679 A1 | 3/2003 | Soll et al. |
| 2003/0055684 A1 | 3/2003 | Jaskolski et al. |
| 2003/0055686 A1 | 3/2003 | Satoh et al. |
| 2003/0065538 A1 | 4/2003 | Abraham-Fuchs et al. |
| 2003/0065740 A1 | 4/2003 | Allen |
| 2003/0069758 A1 | 4/2003 | Anderson et al. |
| 2003/0069759 A1 | 4/2003 | Smith |
| 2003/0074225 A1 | 4/2003 | Borsand et al. |
| 2003/0074227 A1 | 4/2003 | Yu |
| 2003/0078810 A1 | 4/2003 | Cole et al. |
| 2003/0078811 A1 | 4/2003 | Cole et al. |
| 2003/0078812 A1 | 4/2003 | Uchikubo |
| 2003/0078813 A1 | 4/2003 | Haskell et al. |
| 2003/0088440 A1 | 5/2003 | Dunn |
| 2003/0088441 A1 | 5/2003 | McNerney |
| 2003/0093296 A1 | 5/2003 | Lee et al. |
| 2003/0093299 A1 | 5/2003 | Kuth et al. |
| 2003/0093301 A1 | 5/2003 | Chesney et al. |
| 2003/0101076 A1 | 5/2003 | Zaleski |
| 2003/0110059 A1 | 6/2003 | Janas, III et al. |
| 2003/0120134 A1 | 6/2003 | Rao et al. |
| 2003/0120512 A1 | 6/2003 | Dengler |
| 2003/0120515 A1 | 6/2003 | Geller |
| 2006/0023580 A1 | 2/2006 | He et al. |

\* cited by examiner

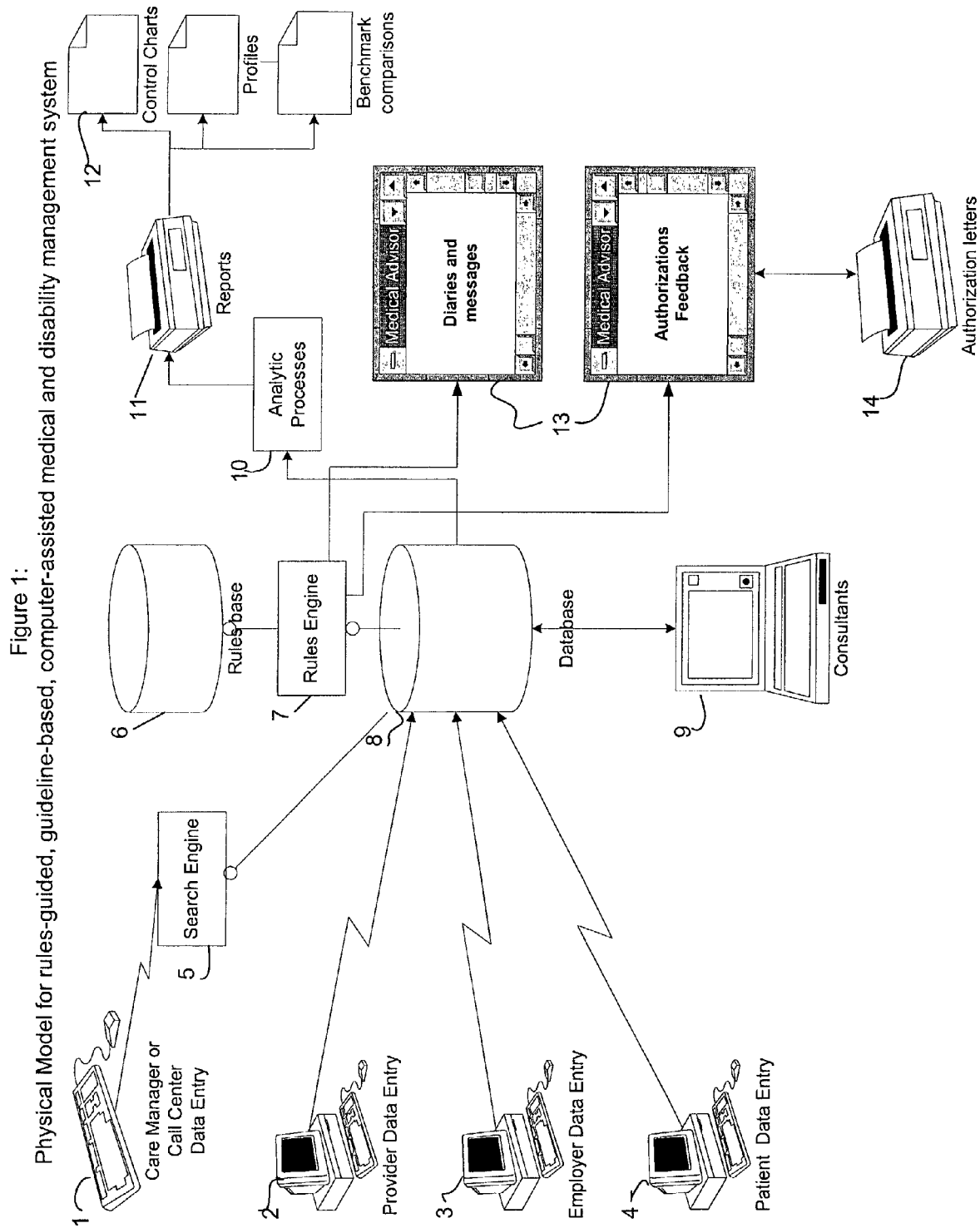

Input process for rules-guided, guideline-based, computer-assisted medical and disability management system Process for rules-guided, guideline-based, computer-assisted medical and disability management system Output and Improvement of Rules-guided, Guideline-based, Computer-assisted Medical and Disability Management System

METHOD FOR ANALYZING RECORDS IN A DATA BASE

BACKGROUND

This invention relates to the evaluation and management of health problems and related disabilities. More particularly, this invention relates to the use of integrated structured methods, information systems, decision rules and practice guidelines to improve outcomes.

The present processes of medical diagnosis, treatment, and management of functional recovery are inconsistent. Often, the processes used for different individuals having similar health problems will vary significantly, yielding different results for each individual. Problems with the acquisition, recording, sharing, storage, comparison, and use of health and functional data underlie much of the observed inconsistency as detailed in the recent National Institute of Medicine reports on health care quality, which are hereby incorporated by reference in their entirety. Inconsistent care can be a major cause of medical errors, unnecessary lost time, and unnecessary costs. To the extent that people with health problems seek or receive diagnosis and treatment from a variety of sources or practitioners, the problems can be compounded.

Common problems with medical and disability data can include:
  Incomplete collection of information needed for decision-making
  Vague or incomplete descriptions of mechanisms of injury or illness, symptoms or signs
  Conclusions or labels rather than underlying mechanisms of injury or illness, symptoms and signs
  Illegible recording of data
  Recording in chronological order rather than by problem
  Use of paper records which cannot be easily sequenced, sorted, arrayed, compared, processed, or summarised
  Existence of records in multiple locations
  Lost, misfiled, or inaccessible records Even when electronic medical and disability management record keeping systems are used, common problems can include:
  Storage of data in a manner such that it cannot be easily sequenced, sorted, arrayed, compared, processed, or summarised
  Incompatible record formats or information systems within institutions and among parties involved in managing health or disability to another
  Difficulty transferring information from one party involved in managing health or disability to another Practitioners rely on a knowledge base that was acquired during their initial training, reinforced or changed by experience, as well as continuing education, which is often sporadic and of variable quality itself. Consequently, problems often observed with the process of medical care are not only due to data collection, but can also be due to lack of a systematic approach to each class of health problems. Because comparisons to medical evidence are often not made during the process of care with respect to a class of health problems, errors in diagnosis and treatment result. The usual clinical and medical management approach is not systematic due to failure to compare each situation with validated information about:
  Sensitive and specific, uniquely diagnostic symptoms, signs, manoeuvres and tests
  Proven effective treatments
  The effect of prior tests and treatments
  The history and time course of a health problem
  The context of the patient's health complaints Failure to consider the context and history of a health problem also contributes to variation in care. In making medical decisions, practitioners may not take into account:
  The context and history of health complaints
  Prior health problems and care
  Previous provision and effectiveness of tests and treatment
  The natural history, or course of a problem if untreated, compared to the course if treated
  The course and effectiveness of the body's own healing process, sometimes in the face of continued exposures to etiologic factors for disease or injury
  The contribution, or lack thereof, of a patient's own responsibility for health, health behaviours, and compliance with activity and treatment recommendations
  The patient's social and work situation Problems frequently observed in the management of functional disability management include:
  Assumptions that inactivity will enable healing and recovery
  Lack of attention to the typical recovery period for a given health problem
  Lack of attention to the essential physical and mental demands of work or school
  Inattention to the social and work context of functional disability
  Failure to use limited activity at work or school to support functional recovery Finally, most health care systems lack timely and effective methods to measure patient and provider satisfaction with care, or to measure functional outcomes of care and disability management. There is therefore no way to correlate the process of care with its outcomes. Feedback of these data can lead to improvement in care.

Practitioners often do not give patients enough understandable information to make informed decisions about their care and functional recovery. Valid information is not easily available elsewhere. Consequently, patients may ask for ineffective or unnecessary care, or may acquiesce to care or activity restriction that is not in their best interest based on the medical evidence.

In response to variations in care and disability management and consequent unnecessary costs and functional disability, self-insured employers, insurers and other payers have attempted to manage care and disability. They have effectively become part of the health care system. However, the ability of case managers, utilisation review personnel, disease managers, and others acting on behalf of employees or payers to make logical, consistent decisions suffers from the same problems as those confronting health care professionals. Their access to data and consistent processes is in fact often worse, as they are one level removed from health care transactions and are hampered by communication problems.

SUMMARY OF THE INVENTION

In accordance with exemplary embodiments of the present invention, a method for analysing records in a data base which collects predetermined data and creates or appends a record, assigns individual conditions to homogeneous groups, retrieves rules, applies the rules to the data, reviews results generated from applying the rules to the data and generates at least one message.

BRIEF DESCRIPTION OF THE DRAWINGS

In the drawings, the present invention is shown first as a physical representation of information, information repositories, rules and output such as case profiles and reports. Second, the process is shown as a continuing sequence of actions interrelating a number of roles in the medical and disability management process.

FIG. 1 is an exemplary embodiment of the physical components for the guideline-based, rules-guided, computer-assisted medical and disability management system.

DETAILED DESCRIPTION

Figure 2A:
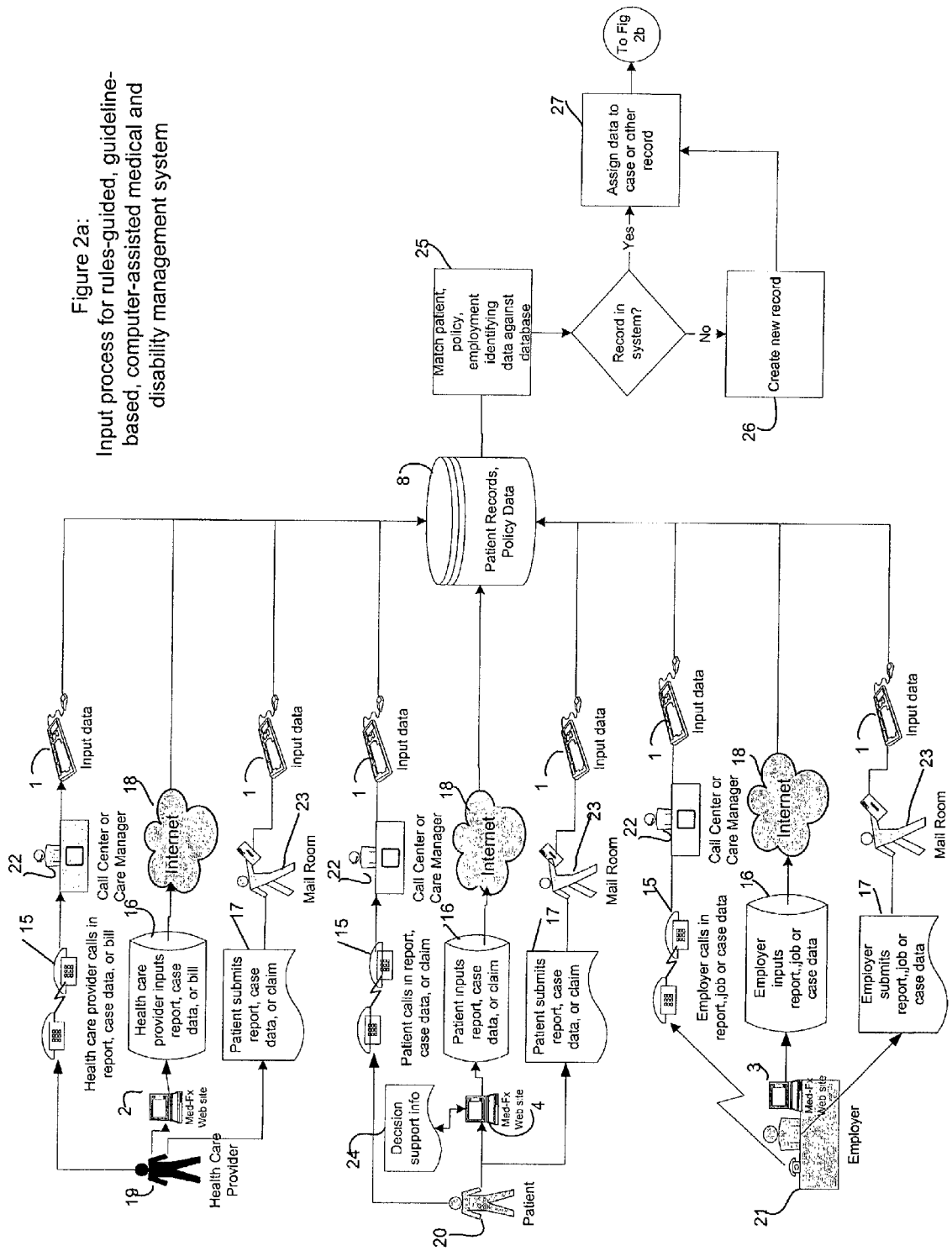
FIG. 2a is an exemplary embodiment of the methods for inputting and indexing data into the electronic database.

An exemplary physical embodiment of the present invention is illustrated in FIG. 1 in a physical model for a rules-guided, guideline-based, computer assisted medical and disability management system. As shown in FIG. 1, the present invention physically includes computer graphic user interfaces or other means of data entry to capture patient information. For example, the patient information can include demographics, employment information, mechanism of injury, etiologic factors of disease, medical history, physical examination data, job data, functional abilities, satisfaction, and other types of information. The patient information can be acquired by call center personnel, care managers 1, or directly from providers' computers or other data entry devices 2. In addition or in the alternative, patient information can also be acquired from employers 3 or from the patients themselves 4. A search engine 5 processes these data to determine if the entity, such as a patient, employer or policy holder has records already stored in a database 8 related to these entities. Additional components are a rules base 6, one or more rules engines 7, analytic processes to analyse output in the aggregate 10, printers 11 to print hard copy reports 12 and display devices to display information to care managers or providers 13, and printers for authorisation letters 14.

Figure 2B:
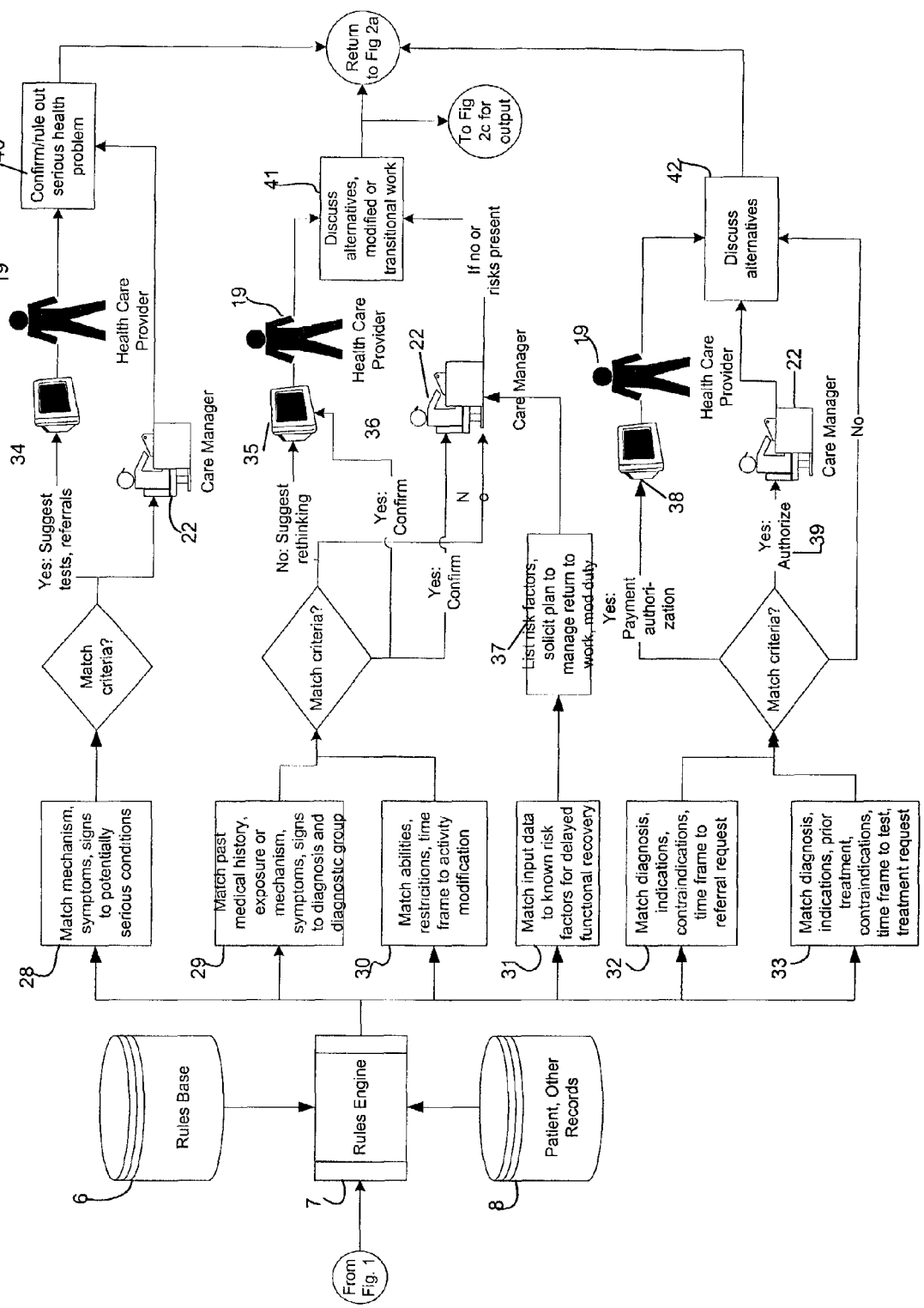
FIG. 2b is an exemplary embodiment of the process followed to compare new and accumulated data to embedded guideline rules, and use the results to reduce errors and variation in care and absence.
Figure 2C:
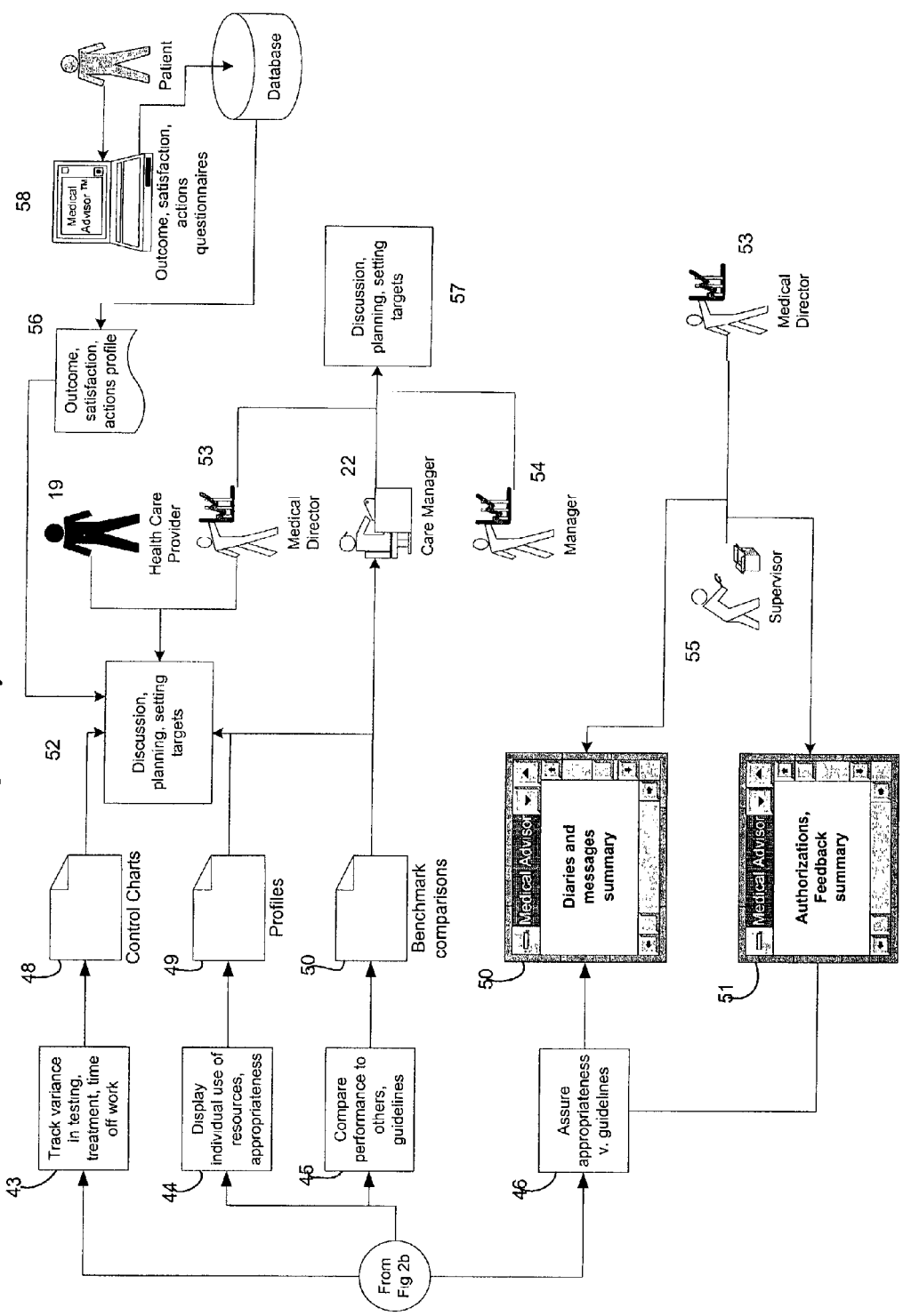
FIG. 2c is an exemplary embodiment of the generation for output from the system by applying descriptive and analytic techniques to the data in the database and collected outcome, action and satisfaction data and reporting the results in actionable form. It also shows use of the reports to facilitate discussion and plan improvements.

A process for using the present invention in accordance with exemplary embodiments is shown in FIG. 2 includes: data input; [demographic data; wherein demographic data comprises; patient name, patient age, patient gender, patient residence, patient education level, patient income, number or names of patient's dependants, patient's spouse name, and spouse's occupation. Health data; wherein health data comprises; current symptoms, mechanism of illness or injury, other current and past medical problems and treatments, previous episodes, outcomes, level of function, satisfaction with care; Occupational and environmental data; wherein occupational and environmental data comprises; occupation, job functions, work and home exposures, work and home psychosocial environment, job satisfaction, work relationships, absence history. Current and past patient medical history, current observations and findings, test results, diagnoses, past observations and treatments, current prescribed treatments, proposed or planned tests or treatments, patient compliance, psychosocial and work factors affecting disability, planned or proposed time off work, activities the patient can perform safely, activities that should be avoided, protective or assistive equipment or devices, a plan of increasing activity to reduce symptoms and restore functional abilities, an analysis of work-relatedness if relevant; Specific incidents or exposures in the workplace: Data for management of disability; wherein data for management of disability comprises; job type, requirements and essential functions, patient income, patient education and training, work relationships and other employment factors, personnel issues, absence history, previous episodes and outcomes records matching or new records creation; matching against guideline-based rules and criteria for scoring questionnaires; return of feedback to providers, care managers and others; discussions or changes in plans if proposed actions or opinions do not match criteria; analysis and display of aggregate resource use, time off work, outcomes, satisfaction, and so on; discussion and planning for improvement; and collection, distribution and discussion of outcome and satisfaction data correlated with care and activity modification.

The manner of using the guideline-based, rules-guided, computer assisted medical and disability management process differs from most processes currently in use. As an overview, the structure of the components described above and the embedded business process result in much less variation in care and disability management, fewer errors, better satisfaction with care, better functional outcomes, and lower costs and risks.

The process starts when a person 20 seeks health care from a health professional 19 or reports a health concern to his or her employer 21 or makes a claim for benefits to a payer 22 by telephone 15, electronically 16 or on paper 17. The health professional 19 then reports case data by telephone 15, to a care manager or payer via a call center 22 or on paper 17, or directly to the application electronically 16, typically via the Internet 18. Paper records and bills can be mailed and received at the payer or care management organisation 23. Telephonic and paper input is entered into the data system by the care manager or someone else at the payer or care management organisation 1. The received data is stored in a database 8. It is matched against existing records 25 so that additional records for existing cases or other records can be appended to those cases 27. If there is no existing case or other record is found, a new record is created 26.

In some instances of the system, an algorithm can be used to separate cases by the likely degree of management needed.

A rules engine 7 then matches collected data against rules for indications for potentially serious medical conditions 28. If any of these indications are present, a message to that effect 34 is sent to the provider, on-line or by other means, and to the care manager 22, if involved in the case. The provider should then order tests or refer the patient to confirm or rule out the presence of such health conditions 40, and treat or refer them. The care manager should ensure that this is done and so note the actions in the database.

The rules engine 7 then matches the past medical history, risks for disease, biological or chemical exposure or mechanism of injury, reported symptoms, physical signs, and provider-diagnosis reported diagnosis to criteria for that diagnosis 29. This process also assigns the diagnosis to a proprietary diagnostic group of synonymous diagnoses, generally those with similar treatment patterns. If the data match the criteria, a message to that effect 36 is sent to the provider and the care manager. If not, a message suggesting rethinking the diagnosis 35 is sent.

The rules engine 7 also matches the patient's current functional abilities, prescription for graded increases in activity, and provider-imposed activity restrictions to guideline-based criteria 30. It is aimed at assisting or supporting functional recovery by providing modified work that does not aggravate the situation but does provide psychosocial support by returning the person to work or school. We are also checking that the provider has prescribed progressive activity to recondition the person and prevent recurrences. Increasing activity relieves pain and other symptoms as well. Activity modification, both initial restriction and later graded increases, is a key element in recovery from many common health problems.

The rules engine 7 compares the data input to known risk factors for delayed functional recovery 31. It compiles a list of any such factors located, and sends a message with the list 37 to the care manager 22 and the health care professional, suggesting that the care manager or provider formulate and input a plan to manage these risks and ensure timely functional recovery.

If a referral is listed in a treatment plan or is requested, the rules engine 7 compares the submitted indications, diagnosis, contraindications, prior tests and treatment, results of prior tests and treatment, and time from the date of onset to guideline-based criteria 32. If the request and associated data match the criteria, a message 38 is sent to the provider stating that the request was appropriate. A similar message 39 suggesting authorising payment for the referral is sent to the care manager, who then makes the authorisation, in the absence of other information to the contrary.

If a significant test or procedure is listed in a proposed treatment plan or requested independently, the rules engine 7 compares the submitted indications, diagnosis, contraindications, prior tests and treatment, results of prior tests and treatment, and time from the date of onset, to guideline-based criteria 33. If the request and associated data match the criteria, a message 38 is sent to the provider stating that the request was appropriate. A similar message 39 suggesting authorising payment for the test or procedure is sent to the care manager, who then makes the authorisation, in the absence of other information to the contrary. If the request does not match criteria, a message to that effect is sent to the provider and the care manager, who should then discuss more appropriate alternatives for testing or treatment 42.

This series of actions 28-33 is repeated for each set of data from a subsequent contact with the health system or as other relevant data become available.

The present invention includes a series of processes to track statistics and match data to provide a quantitative basis for quality improvement. The software application can compile and display reports on variance in resource use and time loss 43, typically control charts, run charts and comparative tables 47; statistics on individual resource use and appropriateness 44, typically provider or care manager profiles 48; and performance comparisons 45, including benchmark comparisons 49. These data can then be used to discuss opportunities for improvement in medical care quality, planning and target setting to measure improvement 52.

The application also generates the comparison messages described above 46, in aggregate and sends them to the supervisor 55 as well as the provider and care manager.

Another aspect of the system is the collection, correlation and feedback of patient surveys of satisfaction and functional and other outcome data 58. Satisfaction and outcome data are indicators of dimensions of medical quality. Outcome data can enhance the research support, or lack thereof, for the effectiveness of various treatments and activity modifications, as well as provider and employer behaviours that enhance or delay functional recovery.

Although the description above contains many specificities, these should not be construed as limiting the scope of the invention but as merely providing illustrations of some of the presently preferred embodiments of this invention. For example, the guideline-based, computer assisted medical and disability management process can use other hardware platforms or software, for example a server installation or palm device.

Thus the scope of the invention should be determined by the appended claims and their legal equivalents, rather than by the examples given.

I claim:

1. A method for analyzing records in a data base comprising:
    collecting predetermined data and searching a data base and creating or appending a record within the data base;
    retrieving rules from a rules base, said retrieved rules selected to correspond to the data base record;
    applying the selected rules or retrieved rules to the data base record;
    reviewing results generated from applying the rules to the data;
    generating at least one message establishing a procedure related to treatment of a medical patient in accordance with the rules;
    storing results of rules application for comparative analysis;
    wherein applying the selected rules further comprises matching a medical patient's physician imposed activity restrictions to guideline-based criteria and wherein the message further comprises suggesting a rethinking of the patient treatment if the medical patient's physician imposed activity restrictions do not match the criteria; and
    wherein the method is executed within a computer system.

2. The method of claim 1 wherein applying the selected rules further comprises matching selected data against rules for indications for potentially serious medical conditions and wherein establishing a procedure further comprises ordering tests to confirm or rule out the serious medical condition.

3. The method of claim 1 further comprising accepting a diagnosis regarding the medical patient and wherein applying the selected rules further comprises matching selected data against criteria associated with the diagnosis and determining if the criteria associated with the diagnosis matches the selected data and wherein the message further comprises confirming the diagnosis if the data matches the criteria and suggesting a rethinking of the diagnosis if the data does not match the criteria.

4. The method of claim 3 wherein applying the selected rules further comprises assigning the diagnosis to a proprietary diagnostic group of synonymous diagnoses with similar treatment patterns.

5. The method of claim 1 wherein the message further comprises suggesting a rethinking of the patient treatment if the medical patient's current functional abilities do not match the criteria.

6. The method of claim 1 wherein applying the selected medical rules that correspond to the data in the medical record further comprises matching a medical patient's prescription for graded increases in activity to guideline-based criteria and wherein the message further comprises suggesting a rethinking of the patient treatment if the medical patient's prescription for graded increases in activity do not match the criteria.

7. The method of claim 1 wherein applying the selected rules further comprises matching submitted indications, diagnosis, contraindications, prior tests and treatment, results of prior tests and treatment, and time from a date of onset, to guideline-based criteria and wherein the message further comprises suggesting a rethinking of the treatment if the medical patient's physician imposed activity restrictions do not match the criteria.

8. The method of claim 1 further comprising storing results of rules application for comparative analysis.

9. The method of claim 1 further comprising generating comparative reports.

10. A method for analyzing records in a data base for managing health problems of medical patients through a computer executed program comprising:
   collecting predetermined data and searching a data base and creating or appending a record within the data base, including receiving the predetermined data about a medical patient needing healthcare and storing the data in a medical record in the data base;
   retrieving rules from a rules base, said retrieved rules selected to correspond to the data base record;
   applying the selected rules or retrieved rules to the data base record by matching the data against medical rules for indications of a medical condition;
   reviewing results generated from applying the rules to the data;
   matching patient's current functional abilities to guideline-based criteria;
   establishing modified recovery work for reconditioning of the patient; and
   generating at least one message establishing a procedure related to treatment of a medical patient in accordance with the rules, including sending the message to a care provider to establish the procedure related to the medical condition when the indications of the medical condition are present;
   wherein applying the selected rules further comprises matching a medical patient's physician imposed activity restrictions to guideline-based criteria, matching patient ability parameters to predetermined guideline-based criteria and establishing modified recovery work for reconditioning of the patient; and the message further comprises suggesting a rethinking of the patient treatment if the medical patient's physician imposed activity restrictions do not match the criteria; and
   wherein the method is executed within a computer system.

* * * * *

UNITED STATES PATENT AND TRADEMARK OFFICE
CERTIFICATE OF CORRECTION

| | | |
|---|---|---|
| PATENT NO. | : 8,560,582 B2 | Page 1 of 1 |
| APPLICATION NO. | : 10/216268 | |
| DATED | : October 15, 2013 | |
| INVENTOR(S) | : Harris | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1207 days.

Signed and Sealed this
Seventeenth Day of May, 2016

Michelle K. Lee
*Director of the United States Patent and Trademark Office*